US008492603B2

(12) United States Patent
Smith et al.

(10) Patent No.: US 8,492,603 B2
(45) Date of Patent: Jul. 23, 2013

(54) SELECTIVATED ISOOLEFIN DIMERIZATION USING METALIZED RESINS

(75) Inventors: Lawrence A. Smith, Pasadena, TX (US); William M. Cross, Seabrook, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 821 days.

(21) Appl. No.: 12/352,198

(22) Filed: Jan. 12, 2009

(65) Prior Publication Data

US 2010/0179362 A1 Jul. 15, 2010

(51) Int. Cl.
*C07C 2/04* (2006.01)

(52) U.S. Cl.
USPC ........... 585/601; 585/515; 585/530; 585/533; 585/510; 502/11; 502/159; 502/12; 502/102; 502/300; 502/301; 502/302

(58) Field of Classification Search
USPC ................. 585/530, 533, 601, 255, 510, 515, 585/520, 521, 526, 310, 316, 511, 512; 502/11, 502/159, 12, 402, 300, 301, 302, 303, 304, 502/305, 306, 307, 308, 309, 310
See application file for complete search history.

(56) References Cited

U.S. PATENT DOCUMENTS

| | | | |
|---|---|---|---|
| 2,366,007 A | 12/1944 | D'Alelio | |
| 3,069,455 A * | 12/1962 | Lum et al. | 558/360 |
| 4,100,220 A | 7/1978 | Bowman et al. | |
| 4,242,530 A | 12/1980 | Smith, Jr. | |
| 4,302,356 A | 11/1981 | Smith, Jr. | |
| 4,313,016 A | 1/1982 | Manning | |
| 4,331,824 A | 5/1982 | Ikeda et al. | |
| 4,375,576 A * | 3/1983 | Smith, Jr. | 585/510 |
| 4,443,559 A | 4/1984 | Smith, Jr. | |
| 4,540,839 A | 9/1985 | Keyworth et al. | |
| 4,551,567 A | 11/1985 | Smith, Jr. | |
| 4,629,710 A * | 12/1986 | Smith, Jr. | 585/639 |
| 4,695,664 A | 9/1987 | Whittle | |
| 4,956,514 A | 9/1990 | Chu | |
| 5,003,124 A | 3/1991 | Smith, Jr. et al. | |
| 5,057,468 A | 10/1991 | Adams | |
| 5,262,012 A | 11/1993 | Smith, Jr. | |
| 5,266,546 A | 11/1993 | Hearn | |
| 5,348,710 A | 9/1994 | Johnson et al. | |
| 5,510,555 A | 4/1996 | Brunelli et al. | |
| 5,730,843 A | 3/1998 | Groten et al. | |

(Continued)

FOREIGN PATENT DOCUMENTS

DE 908247 4/1954

*Primary Examiner* — In Suk Bullock
*Assistant Examiner* — Sharon Pregler
(74) *Attorney, Agent, or Firm* — Osha Liang LLP

(57) ABSTRACT

A process for the dimerization of isoolefins, including: contacting an isoolefin with a solid catalyst composition passivated with at least one of an ether, an alcohol, and water; wherein the solid catalyst composition comprises at least one of a solid phosphoric acid catalyst and a resin of a macroporous matrix of polyvinyl aromatic compound crosslinked with a divinyl compound and having thereon from about 3 to 5 milli equivalents of sulfonic acid groups per gram of dry resin; and wherein at least 50% to less than 100% of acid groups in the solid catalyst composition are neutralized with a metal of Al, Fe, Zn, Cu, Ni, or mixtures thereof. The catalyst may be metalized prior to placement in a reactor or may be metalized in situ.

9 Claims, 2 Drawing Sheets

U.S. PATENT DOCUMENTS

| | | |
|---|---|---|
| 5,877,372 A | 3/1999 | Evans et al. |
| 6,143,942 A | 11/2000 | Verrelst et al. |
| 6,335,473 B1 | 1/2002 | Bakshi et al. |
| 6,376,731 B1 | 4/2002 | Evans et al. |
| 6,501,001 B2 | 12/2002 | Commereuc et al. |
| 6,689,927 B1 | 2/2004 | Frame et al. |
| 6,774,275 B2 | 8/2004 | Smith, Jr. et al. |
| 6,858,770 B2 | 2/2005 | Gelbein et al. |
| 6,936,742 B2 | 8/2005 | Smith, Jr. |
| 6,995,296 B2 | 2/2006 | Smith, Jr. et al. |
| 7,145,049 B2 | 12/2006 | Loescher et al. |
| 7,250,542 B2 | 7/2007 | Smith, Jr. et al. |
| 7,288,693 B2 | 10/2007 | Smith, Jr. et al. |
| 7,319,180 B2 | 1/2008 | Smith, Jr. et al. |
| 2004/0006252 A1 | 1/2004 | Smith |
| 2004/0097773 A1* | 5/2004 | Beckmann et al. ........... 585/530 |
| 2004/0210093 A1 | 10/2004 | Groten et al. |
| 2006/0030741 A1 | 2/2006 | Smith et al. |
| 2007/0161843 A1 | 7/2007 | Smith et al. |
| 2008/0045763 A1 | 2/2008 | Cross et al. |
| 2008/0064911 A1 | 3/2008 | Loescher et al. |

* cited by examiner

SELECTIVATED ISOOLEFIN DIMERIZATION USING METALIZED RESINS

BACKGROUND OF DISCLOSURE

1. Field of the Disclosure

Embodiments disclosed herein relate generally to a process for the dimerization of isoolefins. More specifically, embodiments disclosed herein relate to processes for the selective dimerization of isoolefins using a metalized resin catalyst.

2. Background

Isobutene is commercially significant in many applications. For example, isobutene is one of the comonomers in butyl rubber. Isobutene can also be oligomerized to produce compounds that can be used as chemical feedstock for further reacting or in gasoline blending. Diisobutene, the isobutene dimer, is of particular commercial value in several applications. For example, diisobutene can be used as an alkylation reaction feedstock or as an intermediate in the preparation of detergents. Diisobutene can also be hydrogenated to pure isooctane (2,2,4 tri-methyl pentane) that is highly preferred in gasoline blending.

Isoolefin oligomerization is a catalytic reaction that uses an acid catalyst. For example, oligomerization of isoolefins has been disclosed in U.S. Pat. Nos. 4,242,530, 4,375,576, 5,003,124, and 7,145,049, 6,335,473, 6,774,275, 6,858,770, 6,936,742, 6,995,296, 7,250,542, 7,288,693, 7,319,180, 6,689,927, 6,376,731, 5,877,372, 4,331,824, 4,100,220 and U.S. Patent Application Publication Nos. 20080064911, 20080045763, 20070161843, 20060030741, 20040210093, and 20040006252, among others. Acid resin catalysts have also found use in various other petrochemical processes, including formation of ethers, hydration of olefins, esterifications, and expoxidations, such as described in U.S. Pat. Nos. 4,551,567 and 4,629,710.

When an isoolefin, in particular isobutene, is oligomerized, it is desired to limit the progress of the oligomerization reaction to the dimer stage. High dimer selectivity may be achieved by adding suitable moderator to the reaction mixture, for example, a certain polar component. Typically, oxygenates, such as water, primary, secondary and tertiary alcohols and ethers, are used as the moderator. Use of MTBE as a reaction moderator, for example, is disclosed in U.S. Pat. No. 4,375,576. U.S. Pat. No. 6,376,731 discloses use of tertiary butanol as a reaction moderator.

The presence of various water soluble or aqueous components used as reaction moderators, such as water, alcohols, and ethers, and operation of reactors at elevated temperatures may result in acid groups being removed from the catalyst (sometimes referred to as "acid throw"). The loss of acid from the solid catalyst may cause a low pH aqueous phase, often resulting in corrosion of reactor vessels and associated piping due to the acid.

Accordingly, there exists a continuing need for isoolefin dimerization catalysts and processes that may decrease or eliminate unwanted corrosion due to loss of acid from a catalyst.

SUMMARY OF THE DISCLOSURE

In one aspect, embodiments disclosed herein relate to a process for the dimerization of isoolefins, including: contacting an isoolefin with a solid catalyst composition passivated with at least one of an ether, an alcohol, and water; wherein the solid catalyst composition comprises at least one of a solid phosphoric acid catalyst and a resin of a macroporous matrix of polyvinyl aromatic compound crosslinked with a divinyl compound and having thereon from about 3 to 5 milli equivalents of sulfonic acid groups per gram of dry resin; and wherein at least 50% to less than 100% of acid groups in the solid catalyst composition are neutralized with a metal of Al, Fe, Zn, Cu, Ni, or mixtures thereof.

In another aspect, embodiments disclosed herein relate to a process for the dimerization of isoolefins, the process including: disposing at least one of a sulfonated macroporous resin catalyst and a solid phosphoric acid catalyst in a reactor; metalizing the at least one of a sulfonated macroporous resin catalyst and a phosphoric acid catalyst with at least one of a metal ion of Groups 4-12 of the Periodic Table, the rare earth metals, and mixtures thereof; feeding an isoolefin and a reaction moderator comprising at least one of an ether, an alcohol, and water to the reactor; contacting the isoolefin with the metalized sulfonated macroporous resin to react at least a portion of the isoolefins to form isoolefin dimers; recovering a reactor effluent comprising the isoolefin dimers.

Other aspects and advantages will be apparent from the following description and the appended claims.

DETAILED DESCRIPTION

Figure 1:
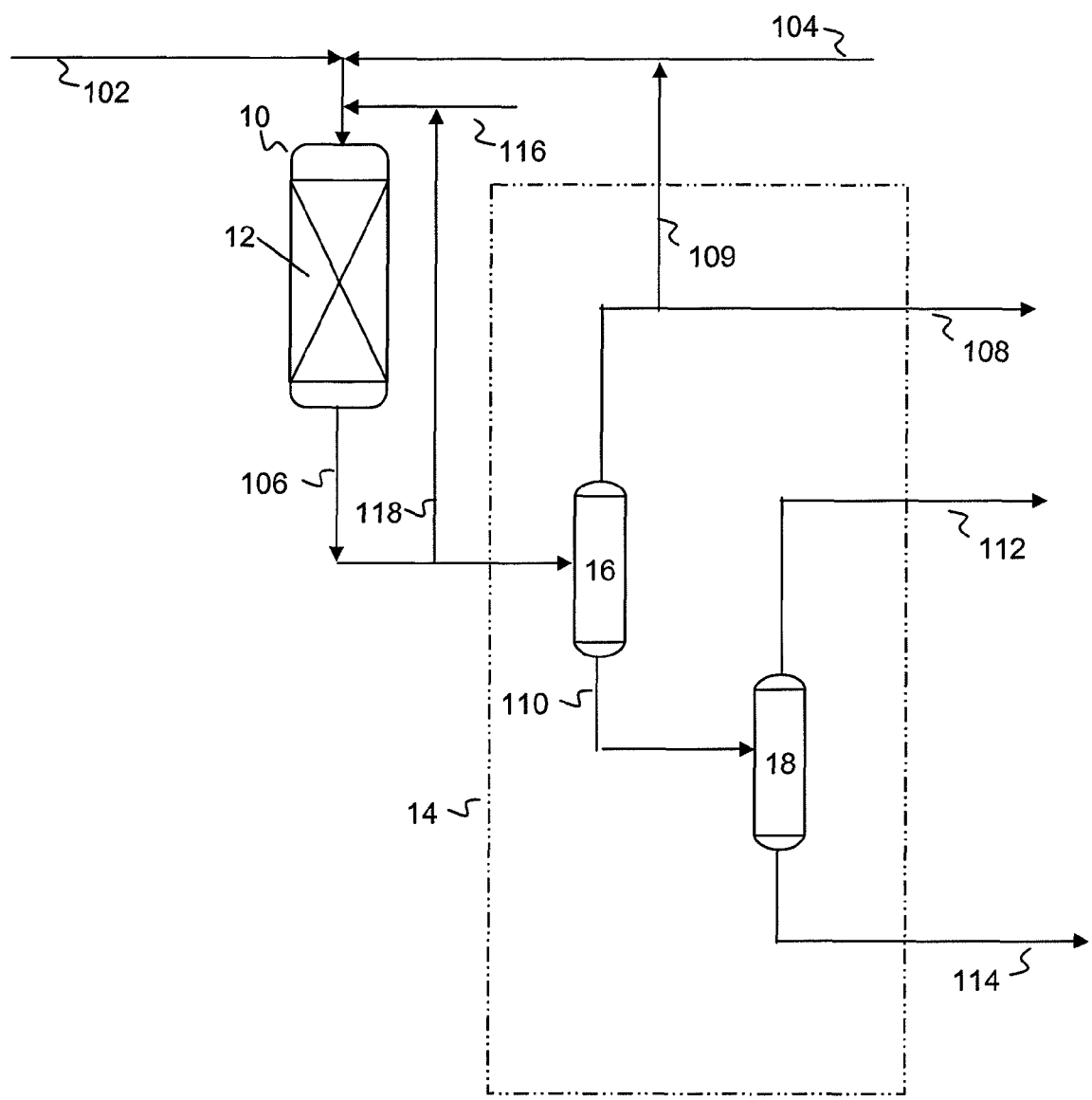
FIG. 1 is a simplified process flow diagram of an isoolefin dimerization process using a metalized resin according to embodiments disclosed herein.

In one aspect, embodiments herein relate to the dimerization of isoolefins. More specifically, embodiments disclosed herein relate to processes for the selective dimerization of isoolefins using a metalized resin catalyst.

Oligomerization may be carried out, for example, in a liquid or partial liquid phase in the presence of a metalized acid cation resin catalyst, either in straight pass type reaction, such as that disclosed in U.S. Pat. Nos. 4,313,016, 4,540,839, 5,003,124, and 6,335,473, or in a catalytic distillation reaction, where there is both a vapor and a liquid phase and a concurrent reaction/fractionation. Isoolefins that may be oligomerized may include isobutene, isopentenes (isoamylenes), and combinations thereof, which are more reactive than n-olefins, and may be selectively oligomerized.

The feed to the oligomerization reactor may include purified isoolefin streams, such as a feed stream containing, propylene, isobutane, isoamylenes, or mixtures thereof. In other embodiments, oligomerization feeds may include a $C_4$-$C_5$, $C_4$ or $C_5$ light naphtha cut. When present in mixtures, the tertiary olefins, such as isobutene and isoamylenes, are more reactive than the normal olefin isomers and are preferentially oligomerized. The primary oligomerization products are dimers and trimers of the $C_3$ to $C_5$ olefins. The isoalkanes in the $C_4$ to $C_5$ light naphtha cut may include isobutane, isopentane or mixtures thereof, as a diluent in the oligomerization reactor.

Oxygen-containing moderators may be used to influence the selectivity of the oligomerization reaction to the dimer product. Oxygen-containing moderators useful in embodiments disclosed herein may include water as well as primary, secondary and tertiary alcohols and ethers. For example, the oxygen-containing moderator may include at least one of: water, tertiary butyl alcohol, methanol, methyl tertiary butyl ether, ethanol, and ethyl tertiary butyl ether.

The primary oligomer products may include dimers and trimers of isoolefins. For example, isobutene may be oligomerized to form a $C_8$ or $C_{12}$ tertiary olefin, isopentene may be oligomerized to form a $C_{10}$ or $C_{15}$ tertiary olefin, and mixtures of isobutene and isopentene may be reacted to form $C_8$ to $C_{15}$ tertiary olefins, among other products. $C_6$ to $C_{16}$ olefin oligomers may also be prepared from $C_3$ to $C_5$ olefins. In some embodiments, the oligomers have 8 to 16 carbon atoms and correspond to oligomers which are prepared from $C_4$ to $C_5$ olefins. The oligomerization of the tertiary olefin may also be performed when carried out on a light naphtha stream with the separation of normal olefins being easily achieved by fractionation from the heavier (higher boiling) oligomers (mainly dimers and trimers).

Selective dimerization may be performed using metalized acid cation resin catalysts as disclosed herein along with reaction moderators, which may be used to passivate and promote the selectivity of the catalyst toward the dimer. Catalysts used in oligomerization reactors may include metalized acid resins, such as AMBERLYST 15 or related oleum derived resins and may include phosphoric acid derived catalysts, such as those known to the industry as SPA (solid phosphoric acid) catalysts. The metalized acid resins are described in more detail below.

Metalized resins according to embodiments disclosed herein, in addition to high selectivity to the dimer product, may reduce throw of acid from a catalyst particle, even at high temperatures and in the presence of an aqueous reaction moderator, such as water, ethers, and alcohols. The reduced loss of acid from the catalyst using metalized resins according to embodiments disclosed herein may thus result in decreased corrosion of reactors and associated equipment that may come into contact with reactor effluent streams.

The oligomerization reactors used in embodiments disclosed herein may include any physical devices or a combination of two or more devices. The reactors may have various internal devices for vapor-liquid separation and vapor/liquid traffic. Any type of reactor may be used to carry out the reactions described herein. The examples of reactors suitable for carrying out the reactions involving isoolefin dimerization or oligomerization reactions may include distillation column reactors, divided wall distillation column reactors, traditional tubular fixed bed reactors, bubble column reactors, slurry reactors equipped with or without a distillation column, pulsed flow reactors, catalytic distillation columns wherein slurry solid catalysts flow down the column, or any combination of these reactors. Multiple reactor systems useful in embodiments disclosed herein may include a series of multiple reactors or multiple reactors in parallel for the first reaction zone. A person of ordinary skill in the art would recognize that other types of reactors may also be used.

For example, straight pass oligomerization reactors may be used, such as disclosed in U.S. Pat. Nos. 4,313,016; 4,540,839; 5,003,124; and 6,335,473. The oligomerization of propylene may be carried out, for example, in tubular reactors at 330-485° F. and 1000 to 1215 psig using supported phosphoric acid (sPa), metal complexes (U.S. Pat. Nos. 5,510,555; 4,695,664 and 6,501,001) and various zeolites, especially ZSM-22, ZSM-57 (U.S. Pat. No. 6,143,942) and MCM-22 (U.S. Pat. No. 4,956,514) which has been shown to have favorable characteristics for the oligomerization of propylene at lower pressures and temperatures than the other catalysts. In such straight pass reactors, the effluent from the oligomerization reaction zone may include the oligomers, unreacted propylene and/or isoolefins, oxygen-containing reaction moderators, and oxygenated oligomerization byproducts.

As another example, the oligomerization may be carried out in a catalytic distillation type reaction, such as that disclosed in U.S. Pat. No. 4,242,530 or 4,375,576. During catalytic distillation, the oligomers and the oxygenated oligomerization byproducts may be fractionated from unreacted isoolefins and other light hydrocarbons. The unreacted isoolefins and other light hydrocarbons, when present, may be recovered as an overheads fraction, a fraction of which may also be used as column reflux. The oligomers and oxygenated oligomerization byproducts may be recovered as a bottoms fraction, where the bottoms fraction is herein defined as the reactor effluent from a catalytic distillation column. Depending upon the type of reaction moderator used and the conditions in the distillation column reactor, the oxygen-containing reaction moderator may be recovered with either or both the overheads fraction and the bottoms fraction.

Other processes and reactors that may benefit from the use of metalized resins for performing oligomerization reactions as disclosed herein may include those described in, for example, U.S. Pat. Nos. 6,689,927, 6,376,731, 5,877,372, 4,375,576, 4,302,356, 4,331,824, and 4,100,220, among others.

Metalized Catalysts

Catalysts that may be used in oligomerization reactors and the catalytic distillation reactor system are metalized acid resin catalysts, such as AMBERLYST 15 or related oleum derived resins, and may include phosphoric acid derived catalysts, such as SPA (solid phosphoric acid) catalysts.

In some embodiments, metalized acid resin catalysts according to embodiments disclosed herein, such as sulfonic acid resins and phosphoric acid catalysts, will have at least 50% of the sulfonic acid groups neutralized with one or more metal ions of Groups 4-12 of the Periodic Table, the rare earth metals, or mixtures thereof. The balance of the phosphoric or sulfonic acid groups may be neutralized with an alkali metal or alkaline earth metal, ammonium, or mixtures thereof. The sulfonic acid may be attached to any polymeric backbone. In some embodiments, the metal ions may include one or more of Ti, V, Cr, Mn, Fe, Co, Ni, Cu, Zn, Zr, Nb, Mo, Ru, Rh, Pd, Ag, Cd, Ta, W, Re, Pt, Ce, Nd, Sm, and Eu. Other metal modified resin catalyst compositions are disclosed in U.S. Pat. Nos. 4,551,567 and 4,629,710, each of which are incorporated herein.

Acid cation exchange resins are well known and have a wide variety of uses. The resins are cation exchangers that contain sulfonic acid groups which may be obtained by polymerization or copolymerization of aromatic vinyl compounds followed by sulfonation. Aromatic vinyl compounds suitable for preparing polymers or copolymers are: styrene, vinyl toluene, vinyl naphthalene, vinyl ethylbenzene, methyl styrene, vinyl chlorobenzene, and vinyl xylene. A large variety of methods may be used for preparing these polymers. For example, polymerization alone or in admixture with other monovinyl compounds, or by crosslinking with polyvinyl compounds, such as divinyl benzene, divinyl toluene, and divinylphenylether, among others. The polymers may be prepared in the presence or absence of solvents or dispersing agents, and various polymerization initiators may be used, e.g., inorganic or organic peroxides, persulfates, etc.

The sulfonic acid group may be introduced into these vinyl aromatic polymers by various known methods; for example, by sulfating the polymers with concentrated sulfuric and chlorosulfonic acid, or by copolymerizing aromatic compounds which contain sulfonic acid groups (see e.g., U.S. Pat. No. 2,366,007). Further sulfonic acid groups may be introduced into the polymers which already contain sulfonic acid groups; for example, by treatment with fuming sulfuric acid, i.e., sulfuric acid which contains sulfur trioxide. The treatment with fuming sulfuric acid is preferably carried out at 0 to 150° C. and the sulfuric acid should contain sufficient sulfur trioxide so that it still contains 10 to 50% free sulfur trioxide after the reaction. The resulting products may contain an average of 1.3 to 1.8 sulfonic acid groups per aromatic nucleus. Particularly, suitable polymers containing sulfonic acid groups are copolymers of aromatic monovinyl compounds with aromatic polyvinyl compounds, particularly, divinyl compounds, in which the polyvinyl benzene content is preferably 1 to 20% by weight of the copolymer (see, for example, DE 908,247).

The acid cation exchange resins may have a granular size of about 0.25 to 1 mm, although particles from 0.15 mm up to about 2 mm may be used. The finer catalysts provide high surface area, but also result in high pressure drops through the reactor. The macroreticular form of these catalysts have a much larger surface area exposed and undergo limited swelling in a non-aqueous hydrocarbon medium compared to the gelular catalysts.

The metalized catalysts may be prepared by contacting a macroporous matrix containing a sulfonic acid group, for example, with an aqueous solution of metal salts and solutions of alkali metal salts, alkaline earth metal salts, and/or ammonium salts to neutralize the acid groups. An alternative procedure for the preparation of the metalized cation resin catalyst compositions comprises contacting a sulfonic acid cation exchange resin, e.g., a macroporous matrix of a polyvinyl aromatic compound crosslinked with a divinyl compound and having thereon from about 3 to 5 milli-equivalents of sulfonic acid groups per gram of dry resin, (1) with an aqueous solution of a soluble metal salt as described above, such as Al, Fe, Zn, Cu, Ni, or mixtures thereof, to neutralize at least 50% to less than 100% of the available sulfonic acid groups with metal ions to produce a partially neutralized resin, and (2) thereafter contacting the partially neutralized resin with an aqueous solution containing a soluble compound of an alkali or alkaline earth metal of Groups 1 or 2, of the Periodic Table, or mixture thereof to neutralize the remaining sulfonic acid groups. In the final alkali neutralization step under the alternate procedure, care must be exercised to not contact the partially neutralized resin with a large excess of alkali or alkaline earth metal ions, (a slight excess, up to about 20%, beyond that required to neutralize the residual sulfonic acid groups may be used) as they appear to form double salts or possibly elute the metal ions, which may reduce the activity of the catalyst. Similarly, phosphoric acid catalysts may be neutralized with salts of Al, Fe, Zn, Cu, Ni, or mixtures thereof to neutralize at least a portion of the acid.

Metalized resin catalyst composition useful herein may be characterized as a solid comprising a macroporous matrix of polyvinyl aromatic compound crosslinked with a divinyl compound and having thereon from about 3 to 5 milli-equivalents of sulfonic acid groups per gram of dry resin, wherein at least 50 percent to less than 100 percent of said sulfonic acid groups are neutralized with a metal ion as described above; in other embodiments, at least 59 percent may be neutralized; and from about 70 percent to about 90 percent neutralized in yet other embodiments. Sulfonic acid groups not neutralized with the metal ion may be neutralized with alkali or alkaline earth metal ions of Group 1 or 2 of the Periodic Table, ammonium ions, or mixtures thereof.

The metalized particulate catalysts may be employed by enclosing them in a porous container such as cloth, screen wire, or polymeric mesh. The material used to make the container may be inert to the reactants and conditions in the reaction system. Particles of about 0.1 to 5 mm size or powders up to about ¼ inch diameter may be disposed in the containers. The container used to hold the catalyst particles may have any configuration, such as the pockets disclosed in the commonly assigned patents noted above, or the container may be a single cylinder, sphere, doughnut, cube, tube, or the like.

It is not essential that the spacing component entirely covers the catalyst component. It is only necessary that the spacing component intimately associated with the catalyst component act to space the various catalyst components away from one another as described above. Thus, the spacing component provides in effect a matrix of substantially open space in which the catalyst components are randomly but substantially evenly distributed. One such structure is that shown in U.S. Pat. No. 5,730,843, incorporated by reference herein. In addition, commonly assigned U.S. Pat. Nos. 4,443,559, 5,057,468, 5,262,012, 5,266,546, and 5,348,710 disclose a variety of catalyst structures for this use and are incorporated by reference herein.

In some embodiments, metalized resin catalysts useful for the selective dimerization of isoolefins may include such catalysts as zinc-treated AMBERLYST 15 and iron or copper-treated AMBERLYST 35, among others.

Referring to FIG. 1, a process for oligomerizing isoolefins according to embodiments disclosed herein is illustrated. An isoolefin, such as isobutene, is fed to an oligomerization reaction zone 10 via flow line 102. An oxygen-containing moderator may be fed to oligomerization reaction zone 10 via flow line 104. The isoolefin reacts in the presence of a metalized oligomerization catalyst contained in bed 12 of oligomerization reaction zone 10 to convert a portion of the isoolefin to oligomers, including dimers and trimers. As a side reaction, the moderator may react with a portion of at least one of the isoolefin and the oligomerization products in oligomerization reaction zone 10 to form an oxygenated oligomerization byproduct. Effluent, containing the oligomerization product and the oxygenated oligomerization byproducts, as well as any unreacted moderator and isoolefin, may be recovered from oligomerization reaction zone 10 via flow line 106.

The reaction effluent may then be fed to a separation system 14 to separate the reaction effluent into the desired fractions. For example, the reaction effluent may be fed via flow line 106 to a first distillation column 16 to separate the moderator and unreacted isoolefin from the oligomers and the oxygenated oligomerization byproducts. The unreacted isoolefin and moderator may be recovered as an overheads fraction via flow line 108, and the oligomers and oxygenated oligomerization byproducts may be recovered via flow line 110. If desired, the moderator and unreacted isoolefin may be recycled to the oligomerization reaction zone via flow line 109.

The bottoms fraction may then be fed via flow line 110 to a second distillation column 18, where the dimers may be separated from the trimers and the oxygenated oligomerization byproducts. The dimers may be recovered as an overheads fraction from column 18 via flow line 112, and the trimers and oxygenated oligomerization byproducts may be recovered via flow line 114, where each may be used in downstream processes as described above.

In some embodiments, metalized resin catalysts may be formed in situ in reaction zone 10. For example, non-neutralized acid resin catalysts may be loaded into catalyst bed 12. Prior to or concurrent with isoolefin feed, metal salts, such as Al, Zn, Cu, Fe, and Ni salts, may be fed to reactor 10, such as via flow line 116. Adequate dispersal of the metal ions through bed 12 may result in neutralization of 50% or more of the acid sites, as described above. If desired, the remaining acid sites may be neutralized with an alkali or alkaline earth metal, which may also be fed via flow line 116.

In other embodiments, initial operation of reaction zone 12 loaded with non-neutralized catalyst may result in a minor amount of corrosion of reaction vessel 10. The resulting metal ions may be included with the reactor effluent in flow line 108. A low pH aqueous phase or a combined aqueous/hydrocarbon recycle, may then be recycled via flow line 118 in order to neutralize at least 50% of the acid with the metal ions. Such recycle of metal ions may be used alone or in addition to the metal salts fed via flow line 116.

When operating with non-neutralized acid catalysts and an aqueous reaction moderator, the aqueous phase generated may have a pH of less than 3 due to loss of sulfonic acid groups from the catalyst. In contrast, use of metalized resins according to embodiments disclosed herein may result in less acid throw, and an aqueous phase having a pH of at least 4; the aqueous phase may have a pH of at least 5 in other embodiments; and the resulting aqueous phase may have a pH of between 6 and 8 in yet other embodiments, when using metalized resins according to embodiments disclosed herein. As a result of the higher pH in the resulting aqueous phase, corrosion of reaction zone 12 and associated equipment may be decreased or eliminated using metalized resins according to embodiments disclosed herein.

Similarly, acid resin catalysts may be metalized in situ in various other types of reactors. For example, when an acid resin catalyst is disposed in a distillation column reactor, metal salts and/or recycle containing metal ions may be fed to the distillation column at an appropriate location to contact the acid catalyst with the metals to neutralize the acid groups and produce the metalized resin catalyst.

The resulting dimer fraction may be used, for example, as a raw material for the production of various chemicals, such as herbicides and pesticides. In other embodiments, the dimer may be fed to an alkylation system, where the dimer may dissociates into constituent olefins and react with an alkane to produce an alkylate in the gasoline-boiling range. The dimer may also be hydrogenated to form gasoline-range hydrocarbons, such as octane, nonane, and other hydrocarbons. In yet other embodiments, the dimer containing stream may be used as a gasoline-range hydrocarbon blendstock without hydrogenation or alkylation.

The recovered heavy fraction, including the trimers, oxygenated oligomerization byproducts, and any other heavy components present, may be used as a blendstock for diesel fuel. The heavy fraction recovered according to embodiments disclosed herein may meet diesel fuel specifications, including being low in sulfur content and having a high flash point.

Oligomerization reactors according to embodiments disclosed herein may include multiple catalyst zones, where one or more catalyst zones may include a metalized catalyst, and where one or more catalyst zones may include non-metalized catalyst. For example, for a distillation column reactor operating with an oxygenate modifier, such as water, placement of the metalized and non-metalized catalyst may be based upon the modifier concentration profile within the reactor. Metalized resin may be used in portions of the column that will be exposed to a high concentration of modifier, thus providing additional stability to catalysts used under such conditions. For portions of the column operating with a low concentration of modifier, non-metalized resin may be used, for example, without resulting in a high acidity (low pH) in product streams recovered from the reactor.

Oligomerizations performed with non-metalized resins are typically conducted at temperatures in the range from about 50° C. to about 120° C. The use of metalized acid catalysts according to embodiments disclosed herein may require use of elevated temperatures to maintain the desired catalyst activity as compared to non-neutralized acid resins. For example, metalized resin catalysts according to embodiments disclosed herein may be used to selectively dimerize isoolefins at temperatures ranging from about 50° C. to about 220° C.; from about 80° C. to about 180° C. in other embodiments.

One skilled in the art may expect use of higher temperatures with a metalized catalyst to result in unwanted polymerization. However, even at the higher temperatures, metalized catalysts according to embodiments disclosed herein exhibit high selectivity toward olefin dimers. For example, selectivity to the dimer may be 80% or greater in some embodiments; 85% or greater in other embodiments; and 90% or greater in yet other embodiments. Use of higher temperatures may additionally result in higher conversion per reactor pass.

Additionally, it may be expected that use of higher temperatures with the acid resin catalysts according to embodiments disclosed herein may result in decreased catalyst life. However, metalized resins according to embodiments disclosed herein exhibit good catalyst stability, even at elevated temperatures. The operational temperature range used may also depend on the metal or metals used to neutralize the acid. For example, Fe-neutralized catalysts may exhibit greater stability at higher temperatures than Cu-neutralized or Zn-neutralized catalysts.

EXAMPLE

Figure 2:
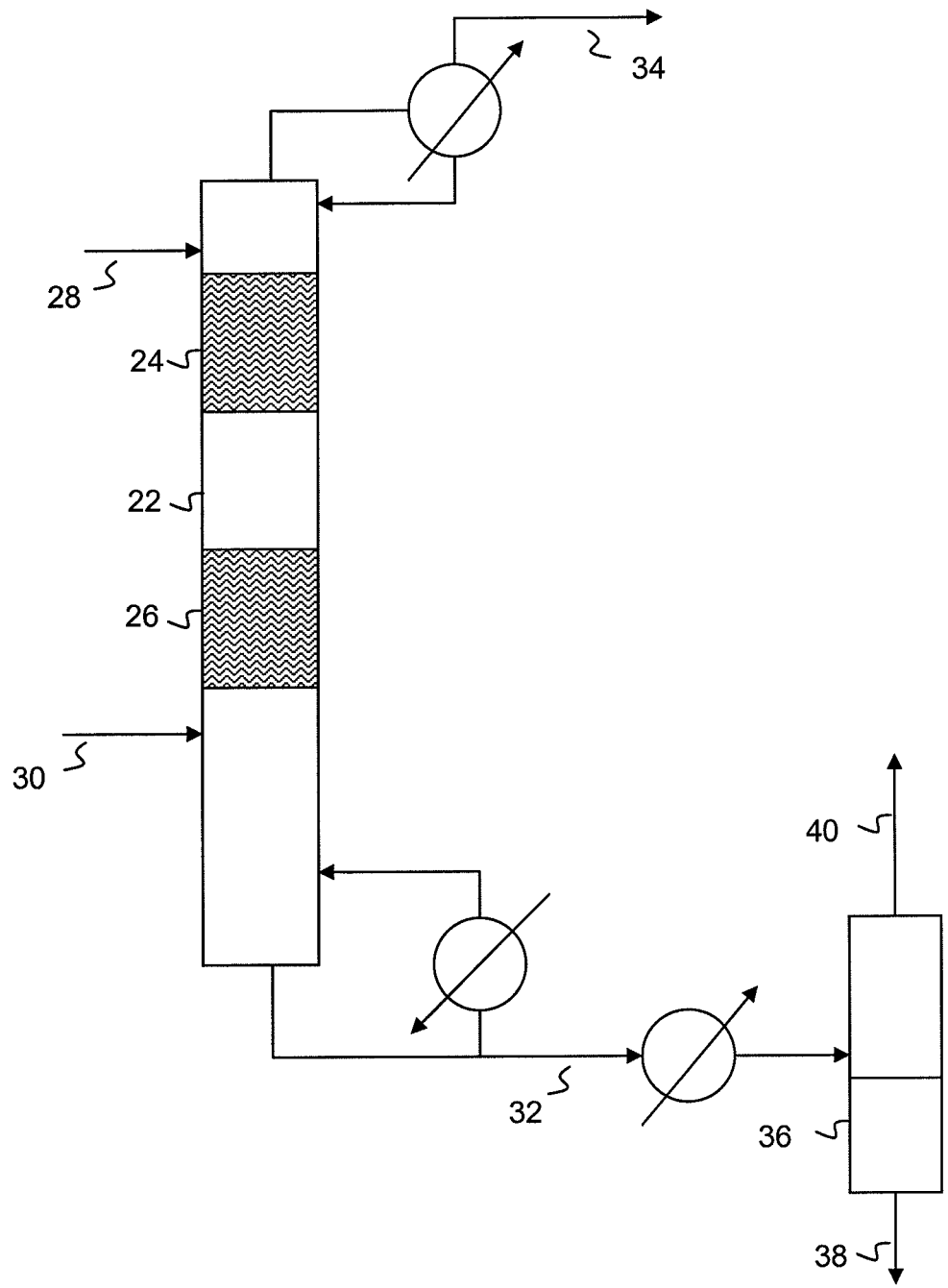
FIG. 2 is a simplified process flow diagram of an isoolefin dimerization process using a metalized resin according to embodiments disclosed herein.

Dimerization with a metalized resin according to embodiments disclosed herein was performed using a reactive distillation system having a flow scheme as illustrated in FIG. 2. A catalytic distillation tower 22 was packed with two sections of catalytically active packing, an upper catalyst zone 24 containing non-metalized Amberlyst A35 and a lower catalyst zone 26 containing metalized Amberlyst A35 resin (copper-neutralized). The lower catalyst zone 26 was metalized to provide catalyst stability, as the amount of oxygenates present within this section is higher than that of the upper zone under distillation conditions used.

A deionized water stream 28 was fed to column 22 above upper catalyst zone 24 at a rate of about 0.32 kg/h (0.7 lb/h). An isobutylene stream 30 was fed to column 22 below lower catalyst zone 26 at a rate of approximately 13.6 kg/h (30 lb/h). The isobutylene was approximately 99.9% wt purity and contained minor amounts of propane. A condition of 99.8% conversion of the isobutylene was achieved using a column overhead pressure of 125 psig while controlling the total unit feed rate and the bottoms temperature. The bottoms temperature was maintained at approximately 210° C. (410° F.), resulting in recovery of a liquid-liquid mixture as a bottoms fraction via flow line 32. The corresponding operating temperature in lower catalyst zone 26 was a top of bed 26 temperature of 71.6° C. (161° F.) and a bottom of bed 26 temperature of 67.2° C. (153° F.). The resulting column products also included an overhead vent 34, a light end purge used to maintain a stable overhead column pressure. Column bottoms fraction 32 contained a mixed two-phase product including a hydrocarbon phase (liquid 1), containing dimer, and a water phase (liquid 2). The column bottoms fraction was fed via flow line 32 to a vertical drum 36 to allow the mixed liquid bottoms stream to settle, providing a clear dimer hydrocarbon product 38 and a bottom aqueous phase 40. The hydrocarbon product 38 included 94.5 wt. % dimer and 5.5 wt. % $C_{12+}$ hydrocarbons (94.5% selectivity to the dimer). The aqueous product 40 had a pH of about 6 and approximately 0.5 wt. % hydrocarbon, including dimer and tertiary butyl alcohol.

As described above, metalized resins according to embodiments disclosed herein may be used to selectively dimerize isoolefins. Advantageously, use of such metalized resins, even in conjunction with aqueous reaction moderators, may result in high selectivity toward the dimer, good catalyst activity, and catalyst stability even at higher reaction temperatures. Additionally, metalized catalysts resins according to embodiments disclosed herein may result in less reactor corrosion as compared to non-metalized acid resin catalysts.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed:

1. A process for the dimerization of isoolefins, comprising:
   contacting an isoolefin with a solid catalyst composition passivated with at least one of an ether, an alcohol, and water;
   recovering a reactor effluent comprising the isoolefin dimers and an aqueous composition;
   wherein the solid catalyst composition comprises at least one of a solid phosphoric acid catalyst and a resin of a macroporous matrix of polyvinyl aromatic compound crosslinked with a divinyl compound and having thereon from about 3 to 5 milli equivalents of sulfonic acid groups per gram of dry resin; and
   wherein greater than 65% to less than 100% of sulfonic or phosphoric acid groups in the solid catalyst composition are neutralized with a metal of Al, Fe, Zn, Cu, Ni, or mixtures thereof,
   wherein a pH of the recovered aqueous composition is greater than about 5.

2. The process of claim 1, wherein the sulfonic or phosphoric acid groups not neutralized with the metal are neutralized with alkali metal ions or alkaline earth metal ions of Group 1 and 2 of the Periodic Table of Elements or mixtures thereof.

3. A process for the dimerization of isoolefins, the process comprising:
   disposing at least one of a sulfonated macroporous resin catalyst and a solid phosphoric acid catalyst in a reactor;
   metalizing the at least one of a sulfonated macroporous resin catalyst and a phosphoric acid catalyst, wherein greater than 65% to less than 100% of the sulfonic or phosphoric acid groups are metalized with a metal of Al, Fe, Zn, Cu, Ni, or mixtures thereof;
   feeding an isoolefin and a reaction moderator comprising at least one of an ether, an alcohol, and water to the reactor;
   contacting the isoolefin with the metalized sulfonated macroporous resin to react at least a portion of the isoolefins to form isoolefin dimers;
   recovering a reactor effluent comprising the isoolefin dimers and an aqueous composition,
   wherein a pH of the aqueous composition is greater than about 5.

4. The process of claim 3, wherein the aqueous composition further comprises Fe ions, the metalizing comprising recycling at least a portion of the aqueous composition to the reactor to neutralize at least a portion of acid groups in the catalyst with the Fe ions.

5. The process of claim 3, wherein the reactor comprises at least one of a distillation column reactor system, a fixed bed reactor, a fluidized bed reactor, a boiling point reactor, and an ebullated bed reactor.

6. The process of claim 3, wherein the contacting is performed at a temperature in the range from about 50° C. to about 220° C.

7. The process of claim 3, wherein the pH of the recovered aqueous phase is in the range from about 6 to about 8.

8. The process of claim 3, further comprising neutralizing at least a portion of sulfonic acid groups not neutralized with the metal with alkali metal ions or alkaline earth metal ions of Group 1 and 2 of the Periodic Table of Elements or mixtures thereof.

9. The process of claim 3, wherein the reaction moderator comprises at least one of water, tertiary butyl alcohol, methanol, methyl tertiary butyl ether, ethanol, and ethyl tertiary butyl ether, and combinations thereof.

* * * * *